United States Patent
Miller, III et al.

(10) Patent No.: US 9,060,229 B2
(45) Date of Patent: Jun. 16, 2015

(54) LOW NOISE ELECTRET MICROPHONE

(75) Inventors: Scott Allan Miller, III, Lafayette, CO (US); Denis Dupeyron, Broomfield, CO (US)

(73) Assignee: Cochlear Limited, Macquarie University, NSW (AU)

(*) Notice: Subject to any disclaimer, the term of this patent is extended or adjusted under 35 U.S.C. 154(b) by 880 days.

(21) Appl. No.: 13/075,813

(22) Filed: Mar. 30, 2011

(65) Prior Publication Data

US 2011/0243350 A1 Oct. 6, 2011

Related U.S. Application Data

(60) Provisional application No. 61/319,168, filed on Mar. 30, 2010.

(51) Int. Cl.
| | |
|---|---|
| H04R 25/00 | (2006.01) |
| H04R 23/00 | (2006.01) |
| H04R 19/01 | (2006.01) |
| A61N 1/36 | (2006.01) |

(52) U.S. Cl.
CPC ............ *H04R 23/006* (2013.01); *H04R 19/016* (2013.01); *A61N 1/36032* (2013.01); *H04R 25/554* (2013.01); *H04R 25/606* (2013.01); *H04R 2225/67* (2013.01); *H04R 2410/03* (2013.01); *H04R 2460/13* (2013.01)

(58) Field of Classification Search
CPC ...... H04R 19/00; H04R 19/01; H04R 19/005; H04R 19/016
USPC .......................................... 381/191, 150, 312
See application file for complete search history.

(56) References Cited

U.S. PATENT DOCUMENTS 3,118,022 A 1/1964 Sessler et al.
3,436,492 A * 4/1969 Reedyk .......................... 381/175

(Continued)

FOREIGN PATENT DOCUMENTS

| EP | 1259094 A2 | 11/2002 |
|---|---|---|
| WO | 2006/076531 A2 | 7/2006 |
| WO | 2006/095946 A1 | 9/2006 |

OTHER PUBLICATIONS

T. Koch, "Design of Micropower Microphone and Speech Detector Circuits," pp. 7-22, ETH Zurich, 2008.*

*Primary Examiner* — Duc Nguyen
*Assistant Examiner* — Kile Blair
(74) *Attorney, Agent, or Firm* — Lowe Hauptman & Ham, LLP

(57) ABSTRACT

An electret microphone having reduced noise due to reduced leakage current is provided. The microphone includes a flexible diaphragm, and sensor member disposed in opposing, spaced relation to the diaphragm and comprising a semiconductor channel. At least one electret surface, comprised of a dielectric material having a permanently-embedded static electric charge, is disposed on one of the diaphragm and the sensor member. In turn, the semi-conductor channel of the sensor member has an electrical conductivity dependent upon relative movement of the diaphragm and support member responsive to acoustic signals incident upon the diaphragm, wherein the channel provides an output signal indicative of the acoustic signals. The electret surface may be disposed on the diaphragm. Alternatively, the electret surface may be disposed on the sensor member in spaced, face-to-face relation to an electrically conductive surface located on the diaphragm.

13 Claims, 3 Drawing Sheets

(56) References Cited

U.S. PATENT DOCUMENTS

| | | | |
|---|---|---|---|
| 3,821,492 | A | 6/1974 | Tamura et al. |
| 3,835,264 | A | 9/1974 | Overby |
| 3,946,422 | A | 3/1976 | Yagi et al. |
| 4,188,513 | A | 2/1980 | Morrell et al. |
| 4,329,547 | A | 5/1982 | Imai |
| 4,447,678 | A | 5/1984 | Fidi |
| 4,922,471 | A | 5/1990 | Kuehnel |
| 5,097,515 | A * | 3/1992 | Baba .................... 381/191 |
| 5,101,543 | A | 4/1992 | Cote et al. |
| 5,859,916 | A * | 1/1999 | Ball et al. .................. 381/326 |
| 5,862,239 | A | 1/1999 | Kubli et al. |
| 5,881,158 | A | 3/1999 | Lesinski et al. |
| 6,093,144 | A | 7/2000 | Jaeger et al. |
| 6,422,991 | B1 | 7/2002 | Jaeger |
| 6,516,228 | B1 | 2/2003 | Berrang et al. |
| 6,626,822 | B1 | 9/2003 | Jaeger et al. |
| 6,648,813 | B2 | 11/2003 | Zilberman et al. |
| 6,694,032 | B2 | 2/2004 | Yun et al. |
| 6,707,920 | B2 | 3/2004 | Miller |
| 6,736,771 | B2 | 5/2004 | Sokolich et al. |
| 6,806,593 | B2 | 10/2004 | Tai et al. |
| 7,003,127 | B1 | 2/2006 | Sujursen et al. |
| 7,065,224 | B2 | 6/2006 | Cornelius et al. |
| 7,136,496 | B2 | 11/2006 | Van Halteren et al. |
| 7,206,423 | B1 * | 4/2007 | Feng et al. .................... 381/312 |
| 7,292,696 | B2 | 11/2007 | Saeki et al. |
| 7,728,779 | B2 * | 6/2010 | Korner .................... 343/702 |
| 8,200,339 | B2 * | 6/2012 | Wiskerke et al. ............ 607/57 |
| 8,345,895 | B2 * | 1/2013 | Chen .................... 381/162 |
| 8,448,326 | B2 | 5/2013 | Sinclair |
| 2001/0033670 | A1 | 10/2001 | Tai et al. |
| 2002/0124656 | A1 | 9/2002 | McIntosh |
| 2002/0172385 | A1 | 11/2002 | Tanabe et al. |
| 2003/0035558 | A1 | 2/2003 | Kawamura et al. |
| 2004/0039245 | A1 | 2/2004 | Jaeger et al. |
| 2004/0109579 | A1 | 6/2004 | Izuchi et al. |
| 2005/0084128 | A1 | 4/2005 | Niederdraenk |
| 2005/0261544 | A1 | 11/2005 | Gan |
| 2006/0177083 | A1 | 8/2006 | Sjursen et al. |
| 2006/0218785 | A1 | 10/2006 | Horiuchi et al. |
| 2006/0280320 | A1 | 12/2006 | Song et al. |
| 2007/0098195 | A1 * | 5/2007 | Holmes .................... 381/315 |
| 2009/0163978 | A1 | 6/2009 | Miller, III et al. |
| 2010/0272287 | A1 | 10/2010 | Miller, III |
| 2013/0010988 | A1 | 1/2013 | Miller, III et al. |

* cited by examiner

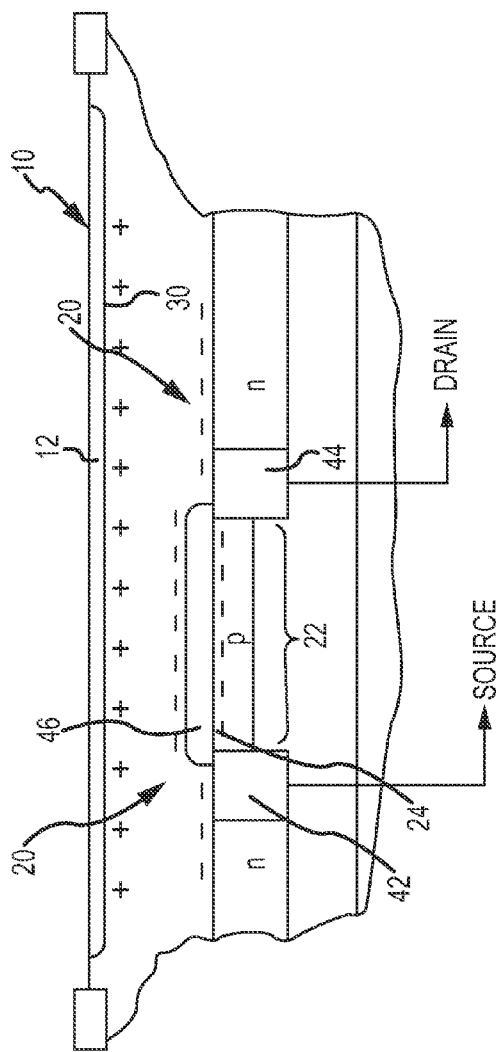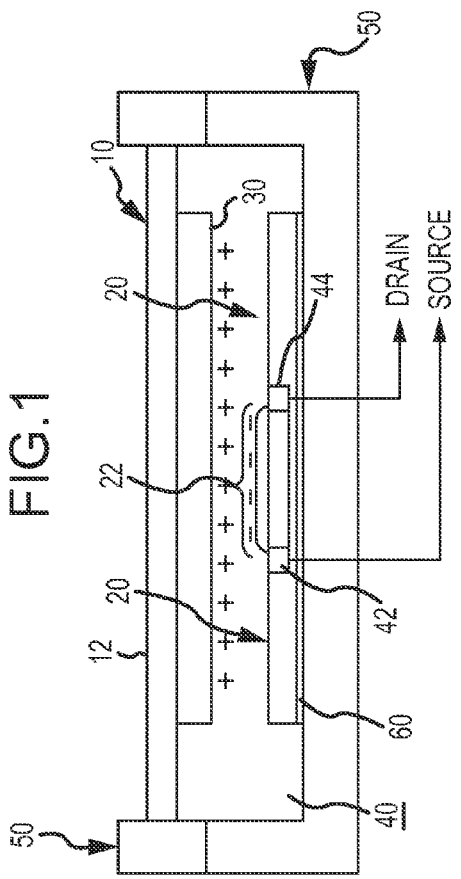

LOW NOISE ELECTRET MICROPHONE

RELATED APPLICATIONS

This application claims priority to U.S. Provisional Application Ser. No. 61/319,168, filed Mar. 30, 2010, entitled "LOW NOISE ELECTRET MICROPHONE", the entirety of which is hereby incorporated by reference.

FIELD OF THE INVENTION

The present invention relates to a low noise electret microphone. The invention is particularly apt for implementation in implantable electret microphones that are employable in fully-implantable and semi-implantable hearing instrument systems.

BACKGROUND OF THE INVENTION

Electret microphones typically include a permanently charged electret and back plate that are capacitively coupled to provide an output signal to an integrated preamplifier that reflects the magnitude of coupling, and in turn, is indicative of the acoustic signals incident upon the microphone. Due to their relatively simple construction, electret microphones offer low profile and compactness advantages. Further, due to relatively recent developments, electret microphones may be produced at a relatively low cost, while also realizing enhanced performance.

In the later regard, a limiting factor for increasing the signal to noise ratio in a typical electret microphone is the presence of a leakage current that passes through an integrated preamplification transistor. The leakage current results from an applied voltage across a semi-conductor channel to a gate of the transistor. Such transistors often utilize silicon oxide insulators between the channel and the gate. However, due to imperfections in the oxide and tunneling effects, leakage currents are still encountered, thereby resulting in undesired noise in the output signal. As may be appreciated, such noise presents particular challenges in hearing instrument applications, and even more particularly, in implanted microphone implementations.

SUMMARY OF THE INVENTION

In view of the foregoing, an objective of the present invention is to provide an electret microphone that may realize an increased signal to noise ratio via a reduction in leakage current present in the microphone.

Another objective of the present invention is to provide a low noise electret microphone that is particularly apt for implementation in conjunction with hearing instrument systems, and in particular implantable arrangements.

The above-noted objectives and additional advantages may be realized in an electret microphone that includes a deflectable diaphragm and a sensor member disposed in opposing, spaced, face-to-face relation to the diaphragm, wherein the sensor member includes a semi-conductor channel. The microphone further comprises an electret surface disposed on one of the diaphragm and sensor member. The electret surface comprises a dielectric material having a permanently-embedded static electric charge, wherein the static charge is employed to induce current flow across the semi-conductor channel indicative of acoustic signals received at the deflectable diaphragm.

In the later regard, the semi-conductor channel of the sensor member may be provided to exhibit an electrical conductivity that is dependent upon relative movement between the diaphragm and sensor member, e.g., deflection of the diaphragm toward the sensor member responsive to acoustic signals incident upon the diaphragm, wherein the channel provides an output signal indicative of the acoustic signals. For example, an n-type semi-conductor arrangement may be employed, wherein an n-type conducting region may form in a p-type semi-conductor material in response to the deflection of a spaced positively-charged surface towards the channel, wherein a current between electrodes disposed on opposite sides of the channel yield an output signal. As may be appreciated, due to the spacing between the flexible diaphragm and the semi-conductor channel of the sensor member, enhanced isolation may be realized, thereby yielding low noise levels in the channel output signal.

In one approach, the electret surface may be disposed on the deflectable diaphragm in face-to-face relation to the semi-conductor channel. In this approach the charged electret surface directly induces current flow across the semi-conductor channel when deflected towards the sensor member.

In another approach, the electret surface may be disposed on the sensor member in spaced, face-to-face relation to a first electrically conductive surface located on the diaphragm. A second electrically conductive surface (e.g., in electrical contact with the first portion) may be disposed in spaced, face-to-face relation to the semi-conductor channel. In this approach, the charged electret surface yields a correspondingly-charged second electrically conductive surface, wherein the charged second electrically conductive surface induces current flow across the semi-conductor channel when deflected towards the sensor member.

In either of the noted approaches, a plurality of electret surfaces may be provided and sized and/or located (e.g., in a predetermined pattern) and/or otherwise permanently charged to different degrees (e.g., differentially charged), wherein the relative size, location and charge levels may be established to enhance and/or attenuate output signal components that correspond with predetermined acoustic signal frequencies. That is, deflection of the diaphragm member may be correlated, at least in part, to different acoustic frequency components causing vibration across the lateral extent of the diaphragm, wherein selected frequency components may be enhanced, or weighted, in the microphone output signal by sizing and/or locating (e.g., patterning) and/or charging the electret surfaces so as to induce greater current flow across predetermined semi-conductor channel regions spatially aligned with predetermined diaphragm regions having vibratory output that correlates with the predetermined frequencies to be enhanced.

In another aspect, the electret microphone may further comprise a hermetically-sealed, enclosed volume, wherein the diaphragm and sensor member define an insulative space therebetween (e.g., air-filled) that is disposed within the enclosed volume. As may be appreciated, such an arrangement may be advantageously employed in implant applications.

In one implantable electret microphone embodiment, a single deflectable diaphragm may be employed, wherein a deflectable biocompatible diaphragm may be sealably disposed across an opening of the housing to define a peripheral portion of the enclosed volume. One or more electret surface(s) may be located on the first diaphragm surface to directly induce current flow across a semi-conductor channel as discussed hereinabove. Alternatively, one or more electret surface(s) may be located on a sensor member and first and second electrically-conductive surface portions (e.g., adjacent portions of a continuous surface) may be located on the first diaphragm to combinatively induce current flow across a semi-conductor channel of the sensor member, as noted above.

In another embodiment, a deflectable membrane may extend across a housing opening to define the enclosed volume, and the deflectable diaphragm may extend across the enclosed volume to define a first portion of the enclosed volume on a first side of the diaphragm (e.g., between the diaphragm and the membrane) and a second portion of the enclosed volume on a second side of the diaphragm (e.g., between the diaphragm and the sensor member). One or more electret surface(s) may be located on the second diaphragm surface to directly induce current flow across a semi-conductor channel as discussed hereinabove. Alternatively, one or more electret surface(s) may be located on a sensor member and first and second electrically-conductive surface portions (e.g., adjacent portions of a continuous surface) may be located on the diaphragm to combinatively induce current flow across a semi-conductor channel, as noted above.

In conjunction with this embodiment, at least one vent may be provided to fluidly interconnect the first portion and the second portion of the enclosed volume. By way of example, the vent(s) may extend through the diaphragm.

In yet a further aspect, the electret microphone may comprise a plurality of semi-conductor channel portions or channels, each such portion or channel having a corresponding separate output. In turn, the plurality of outputs may be employed separately (e.g., amplified) to weight predetermined frequency components of acoustic signals received at the diaphragm and/or employed separately (e.g., phased) to otherwise provide directional sensitivity in relation to such acoustic signals.

In another aspect, an inventive method is provided for generating microphone output signal indicative of acoustic signals received thereby. The method includes the steps of deflecting a deflectable diaphragm in vibratory response to acoustic signals received thereby, and providing at least one electrically-charged surface on the diaphragm in opposing spaced relation to a semi-conductor channel of a sensor member. The method further includes the step of utilizing the at least one electrically charged surface to induce current flow across the semi-conductor channel in response to the vibratory deflection of the diaphragm, wherein the current provides at least one output signal indicative of the acoustic signals.

The providing step may comprise disposing at least one or a plurality of electret surface(s) on at least one of the diaphragm and the sensor member, wherein the at least one electret surface(s) includes a dielectric material having a permanently-embedded static electric charge. In one approach, the at least one electret surface(s) may be disposed on the diaphragm in opposing spaced relation to the semi-conductor channel. In another approach, the at least one electret surface(s) may be disposed on the sensor member, wherein the diaphragm includes at least one electrically conductive surface portion that defines said at least one electrically charged surface portion in response to the at least one electret surface (s).

In certain implementations, the disposing step may include disposing a plurality of electret surfaces that are sized and/or located (e.g., in a predetermined pattern) and/or otherwise permanently charged to different degrees (e.g., differentially charged), wherein the relative size, location and charge levels may be established to enhance and/or attenuate output signal components that correspond with predetermined acoustic signal frequencies, as described above. The plurality of electret surfaces may be located on the diaphragm or on the surface member, as noted above.

In conjunction with the inventive method, a hermetically-sealed, enclosed volume may be defined, wherein the diaphragm and sensor member define an insulative space therebetween that is disposed within the enclosed volume. In this regard, the volume may be defined by locating the diaphragm across an opening of a housing, wherein the diaphragm defines a peripheral portion of the enclosed volume of the microphone, and wherein the diaphragm and housing are each biocompatible.

In another approach, the enclosed volume may be defined by locating a deflectable membrane across an opening of a housing, wherein the membrane and housing are each biocompatible. In conjunction with this approach, the deflectable diaphragm may be positioned across the enclosed volume (e.g., within the housing) to define a first portion of the enclosed volume between the diaphragm and the membrane, and a second portion of the enclosed volume between the diaphragm and sensor member. In turn, the method may further provide for fluid interconnection of the first portion of the enclosed volume with the second portion of the enclosed volume (e.g., via one or more vents extending through the diaphragm). As may be appreciated, such fluid interconnection allows for gas flow between the first portion and second portion to facilitate pressure equalization in response to ambient pressure variations acting upon the deflectable diaphragm (e.g., due to barometric pressure variations acting upon the deflectable diaphragm). In the later regard, pressure variations may be experienced due to elevational changes (e.g., when a patient travels from sea level to an elevated region).

In a further aspect, the method may further comprise the employment of at least two outputs corresponding with current flow across two different semi-conductor channel portions and/or across two different semi-conductors. In turn, the method may include utilizing the at least two outputs to weight predetermined frequency components and/or provide directional sensitivity in relation to the acoustic signals.

The present invention may be employed in an implantable microphone for use with additional implanted componentry, such as the additional componentry taught by U.S. Patent Application Publication No. 2006/0183965 and U.S. Pat. No. 7,354,394, hereby incorporated by reference in their entireties.

Additional features of the present invention will become apparent to those skilled in the art upon consideration of the further description provided hereinbelow.

BRIEF DESCRIPTION OF THE DRAWINGS

FIG. 1 is a cross-sectional schematic illustration of a first electret microphone embodiment.

FIG. 2 is a cross-sectional, schematic illustration of another electret microphone embodiment adapted for implant use, e.g., use in a semi-implantable or fully-implantable hearing instrument system.

DETAILED DESCRIPTION OF THE DRAWINGS

Figure 3:
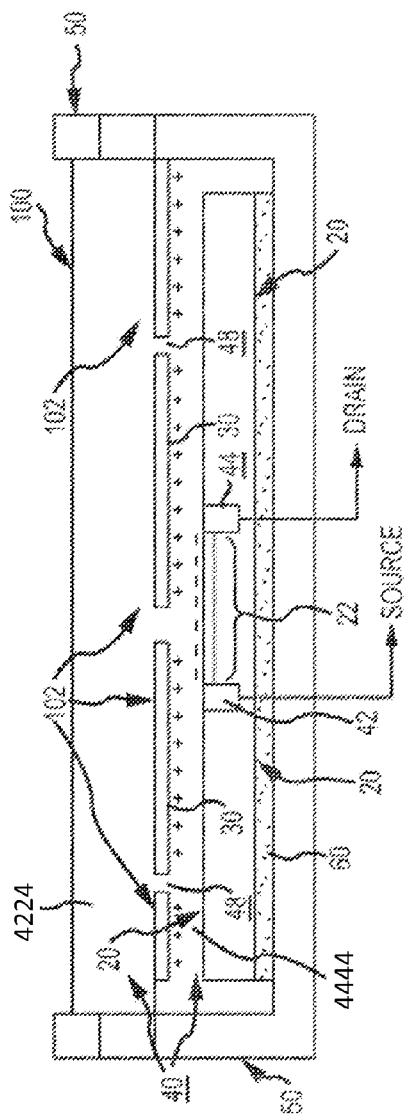
FIG. 3 is a cross-sectional, schematic illustration of another electret microphone embodiment adapted for implant use, e.g., use in a semi-implantable or fully-implantable hearing instrument system.

FIG. 1 is a schematic illustration of an electret microphone embodiment that comprises a deflectable diaphragm 10 disposed in opposing, spaced relation to a sensor member 20. The sensor member 20 includes a semi-conductor channel 22 that may define a portion of a surface of the sensor member 20. In turn, an electret surface 30 may be disposed on the deflectable diaphragm 10 in spaced, face-to-face relation to the surface of the semi-conductor channel 22 of the sensor member 20. The electret surface 30 may comprise a dielectric material having a permanently-embedded static electric charge. As will become apparent, the described arrangement may be analogized to a gateless transistor, wherein deflection of the charged electret surface 30 towards the sensor member 20 yields a responsive current output signal across the semi-conductor channel 22.

In this regard, the deflectable diaphragm 10 may be disposed so as to receive acoustic signals at surface 12 and vibrate in response thereto. In conjunction with such vibration, electret surface 30 may deflect towards/away from the channel 22, wherein the channel 22 may be induced to become larger/smaller and correspondingly more/less conductive. Such change in conductivity may affect a change in the magnitude of an electric current passing between first and second electrodes, 42 and 44, respectively, disposed on opposing sides of the semi-conductor channel 22 and electrically interconnected to a source and drain, respectively, in an interconnected circuit. As may be appreciated, the channel 22 output signal may be indicative of the acoustic signals received at surface 12 of the diaphragm 10.

In the arrangement shown in FIG. 1, the semi-conductor channel 22 is defined by an npn-type semi-conductor arrangement, wherein a conducting n-type region 24 forms in the p-material in response to the proximity of the positively-charged electret surface 30. That is, as the positively-charged dielectric surface 30 moves closer to the surface of channel 22, the depth, or thickness, of the conductive n-type region 24 increases, thereby increasing the magnitude of the current output signal. Conversely, as the electret surface 30 moves away from the surface of channel 22 the depth of the conductive n-type region decreases, thereby decreasing the magnitude of the current output signal. In other embodiments, a pnp-type semi-conductor arrangement may be employed.

As may be appreciated, by disposing the channel 22 so as to extend across a lateral extent of the sensor member 20 in opposing relation to a corresponding lateral extent of the electret surface 30 on diaphragm 10, the output signal may comprise frequency and magnitude components that correspond with the region and degree of vibratory movement, or deflection, of the diaphragm 10 across the corresponding lateral extent thereof in response to acoustic signals received at surface 12 of the diaphragm 10.

In one feature, the electret microphone may be provided so that semi-conductor channel 22 is slightly conductive when the diaphragm 10 is at a predetermined minimum degree of deflection towards the sensor member 20, and so that the current output signal does not exceed a predetermined saturation level when the diaphragm 10 is at a predetermined maximum degree of deflection towards the sensor member 20. As another feature, the semi-conductor channel 22 may be provided so that the current output signal is substantially linearly related to the degree of deflection of the diaphragm 10.

In some embodiments, the semi-conductor channel 22 may comprise silicon and/or germanium, and may be covered by an oxide layer 46. Further, the channel may be doped utilizing a dopant such as boron. The electret surface may comprise a dielectric material such as a fluorine-containing polymer (e.g., Teflon) that is spun-coated on to the diaphragm 10. The doping may be carried out to facilitate the realization of a semi-conductor channel 22 output signal that is substantially linearly related to the degree of deflection of the diaphragm 10 as noted above.

In another feature, a plurality of electret surfaces may be provided in opposing relation to different regions of semi-conductor channel 22. The electret surfaces may be sized and/or located (e.g., in a predetermined pattern) and/or otherwise charged to different charge levels to enhance or attenuate, in a relative sense, different predetermined components of the output signal from channel 22 that correspond with different predetermined frequency components of acoustic signals received at surface 12 of diaphragm 10. As may be appreciated, such acoustic frequencies may be correlated to predetermined offset regions located across the lateral extent of diaphragm 10.

Reference is now made to FIG. 2 which illustrates another embodiment of an electret microphone adapted for implantation and use in connection with a semi-implantable or fully implantable hearing instrument system. By way of example, the hearing instrument system may comprise an implantable cochlear stimulation electrode array for achieving electrical stimulation and/or an implantable bone-contacting transducer for achieving mechanical stimulation of a patient's auditory system. Typically, the microphone output signal may be converted to a digital signal for processing by a speech processor that provides a data signal employable to generate a stimulation signal for activating an interconnected cochlear electrode array or bone-contacting transducer. The speech processor may be disposed in an implantable housing module and operatively interconnected to the microphone auditory stimulation device (e.g., via a flexible signal cable). In some arrangements, an implantable power source may also be disposed in the implantable housing module and operatively interconnected to other implanted componentry to provide power thereto. For example, a rechargeable battery may be provided with an interconnected coil for wireless RF signal receipt/recharging from an external coil/power source.

The implantable electret microphone embodiment of FIG. 2 incorporates features of the embodiment of FIG. 1, and therefore common reference numerals are utilized therein in relation to corresponding components. In this embodiment, the deflectable diaphragm 10 is disposed across an opening of a housing 50, wherein a hermetically-sealed, enclosed volume 40 is defined therewithin. The housing 50 and diaphragm 10 may be biocompatible. For example, the housing 50 and diaphragm 10 may comprise titanium. The electret surface 30 may be defined by a layer of dielectric material applied to the diaphragm 10 As illustrated in FIG. 2, the electret microphone may further comprise an electrically non-conductive layer 60 interposed between the sensor member 20 and the housing 50.

FIG. 3 illustrates another embodiment of an implantable electret microphone that incorporates features of the embodiments of FIGS. 1 and 2. As such, common reference numerals are utilized in relation to corresponding components. In this embodiment, two deflectable diaphragms are employed. A first deflectable diaphragm 100 is disposed across an opening of a biocompatible housing 50, wherein a hermetically-sealed, enclosed volume 40 is defined therewithin. A second deflectable diaphragm 102 is positioned supportably across the enclosed volume 40 between the first deflectable diaphragm 100 and a sensor member 20, wherein a first portion 4224 of the enclosed volume 40 is defined between the first diaphragm 100 and second diaphragm 102, and a second portion 4444 of the enclosed volume 40 is defined between the second diaphragm 102 and the sensor member 20. To facilitate pressure equalization between the first portion 42 and second portion 44, e.g., resulting from biometric pressure variations acting upon the first deflectable diaphragm 100, one or more vents 48 may be provided through the second deflectable diaphragm 102. In this embodiment, an electret surface 30 may be defined by a layer of dielectric material disposed on the second diaphragm 102 in spaced, face-to-face relation to the semi-conductor channel 22 of the sensor member 20.

Figure 4:
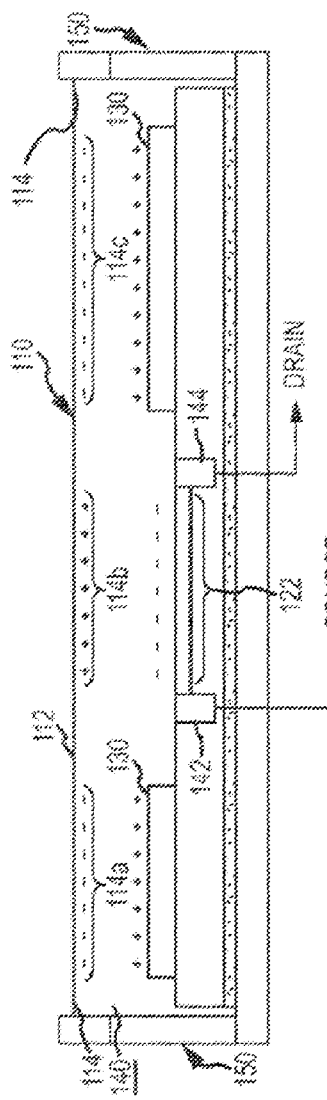
FIG. 4 is a cross-sectional, schematic illustration of another electret microphone embodiment adapted for implant use, e.g., use in a semi-implantable or fully-implantable hearing instrument system.

Reference is now made to FIG. 4 which illustrates another embodiment of an implantable electret microphone. In this embodiment, a deflectable diaphragm 110 may be disposed across an opening of a housing 150 to define an enclosed volume 140, wherein at least an internal facing surface 114 of the deflectable diaphragm 110 may be electrically conductive. A sensor member 120 may be disposed within the enclosed volume and includes a semi-conductor channel 122 having a surface 122a located in spaced, face-to-face relation to the electrically conductive surface 114 of the deflectable diaphragm 110. One or more of electret surface(s) 130 may be disposed on the sensor member 120 in spaced, face-to-face relation to the electrically conductive surface 114 of the deflectable diaphragm 110.

In the illustrated embodiment, a plurality of electret surfaces 130 are defined, each of such surfaces 130 comprising a dielectric material that has been permanently embedded with a positive, static electric charge. In turn, negatively and positively charged regions 114a and 114b, respectively, may be defined on the electrically conductive surface 114 in corresponding spatial relation to the locations of the electret surfaces 130, wherein the magnitude of such positively-charged regions 114b and negatively-charged regions 114a is a function the degree of spacing between the dielectric surfaces 130 and the electrically conductive surface 114.

As illustrated, at least some of the positively-charged regions 114b may be disposed in spaced, face-to-face relation to the surface of 122a of the semi-conductor channel 122. In turn, upon deflection of the diaphragm 110 in response to the receipt of acoustic signals at an external surface 112 of the diaphragm 110, the positively-charged region 114b of the electrically conductive surface 114 may deflect towards the surface of 122a of the semi-conductor channel 122, thereby increasing the conductivity of the channel 122 and correspondingly yielding a current signal across the channel 122 between electrodes 142 and 144, in a manner analogous to the operation of FIG. 1 described hereinabove.

Figure 5:
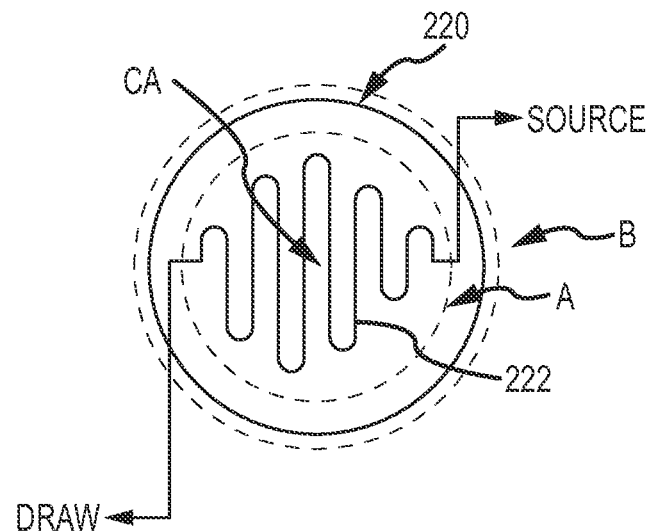
FIG. 5 is a top view of an embodiment of a sensor member having a semi-conductor channel employable in embodiments of the present invention.

Reference is now made to FIG. 5 which illustrates an embodiment of a sensor member 220 having a semi-conductor channel 222 disposed in one pattern employable in any of the above-described embodiments of the present invention. As shown, semi-conductor channel 222 may be disposed in a serpentine pattern to extend back-and-forth across a lateral extent of the sensor member 220, (e.g., so as to have a plurality of channel portions located at different radius and at different angular positions relative to a common center axis CA of the sensor member 220 and an opposing deflectable diaphragm, not shown). As further illustrated, such pattern may be located within an area A (e.g., indicated by phantom lines in FIG. 5) that is relatively large in relation to an aligned area B (e.g., indicated by phantom lines in FIG. 5), reflecting the size and shape of an opposing, deflectable diaphragm having an electret surface(s) or charged electrically conductive surface(s) disposed thereupon to induce current flow across the channel 222, as described in one or more of the embodiments herein above. By way of example, a ratio of A/B may preferably be ≥0.5, while maintaining the desired to aspect ratio of the corresponding electret microphone at a level that may be desirable for realizing a desired resistance.

As may be appreciated, by patterning the semi-conductor channel 222 as illustrated in FIG. 5, the current inducing effect of vibratory motion of a deflectable diaphragm may be maximized. Further, sensitivity across a broad continuum of frequency ranges may be realized.

Figure 6:
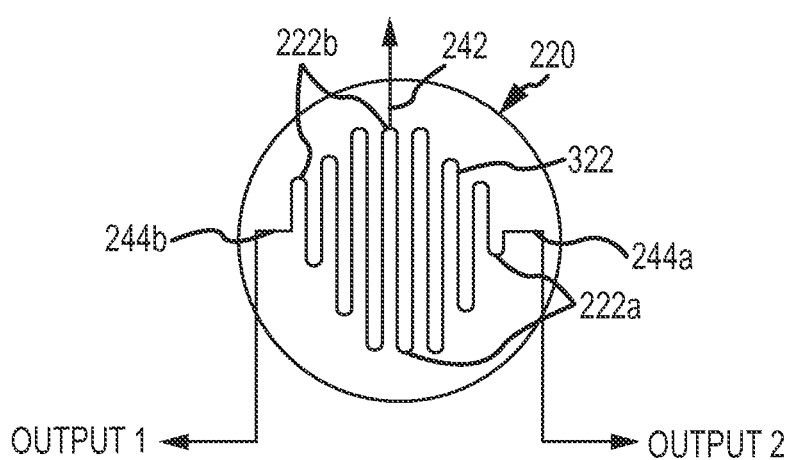
FIG. 6 is a top view of the sensor member embodiment of FIG. 5 with multiple channel portion outputs.

Reference if now made to FIG. 6 which illustrates the sensor member 220 and semi-conductor channel 222 of FIG. 5, wherein multiple channel portions of corresponding outputs are illustrated. More particularly, the semi-conductor channel 222 is provided with a common input electrode 242 and two output electrodes 244a and 244b. In turn, semi-conductor channel 242 operatively comprises a first channel portion 222a and a second channel portion 222b. The outputs at electrodes 244a and 244b may be conditioned and/or processed to provide directional sensitivity and/or otherwise weight acoustic signal components.

Various modifications, adaptations and feature combinations of the above-described embodiments will be apparent to those skilled in the art and are intended to be within the scope of the present invention.

What is claimed is:

1. An electret microphone comprising:
   a flexible diaphragm;
   a sensor member disposed in opposing, spaced relation to said diaphragm and including a semi-conductor channel; and,
   an electret surface comprising a dielectric material having a permanently-embedded static electric charge, said electret being disposed on one of said diaphragm and said sensor member, wherein the channel of said sensor member has an electrical conductivity dependent upon relative movement of the diaphragm and sensor member responsive to acoustic signals incident upon said diaphragm, and wherein the channel provides an output signal indicative of the acoustic signals,
   wherein:
      said electret surface is disposed on said diaphragm in spaced, face-to-face relation to said channel; or
      said electret surface is disposed on said sensor member in spaced, face-to-face relation to an electrically conductive surface located on said diaphragm and disposed in spaced, face-to-face relation to said channel.

2. The electret microphone of claim 1, wherein said channel defines a first surface portion of the sensor member, and wherein said electret surface is disposed on a second surface portion of the sensor member that is spaced from said first portion thereof.

3. The electret microphone of claim 1, wherein said channel extends across a surface of the sensor member in a non-linear, predetermined configuration.

4. The electret microphone of claim 3, wherein said predetermined configuration is a serpentine configuration.

5. The electret microphone of claim 1, further comprising:
   a plurality of electret surfaces each having a permanently embedded static charge and being at least one of sized, located and differentially charged to weight predetermined frequency range components of said output signal.

6. The electret microphone of claim 1, said sensor further comprising:
   a plurality of semi-conductor channel portions having corresponding outputs, wherein said outputs may be separately employed to weight predetermined frequency range components of said output signal.

7. The electret microphone of claim 1, further comprising a hermetically-sealed, enclosed volume, wherein the diaphragm and sensor member define an air-gap therebetween that is disposed in the enclosed volume.

8. An electret microphone comprising:
   a flexible diaphragm;
   a sensor member disposed in opposing, spaced relation to said diaphragm and including a semi-conductor channel;
   a hermetically-sealed, enclosed volume, wherein the diaphragm and sensor member define a space therebetween that is disposed between the enclosed volume; and,
   an electret surface comprising a dielectric material having a permanently-embedded static electric charge, said electret being disposed on one of said diaphragm and said sensor member, wherein the channel of said sensor member has an electrical conductivity dependent upon relative movement of the diaphragm and sensor member responsive to acoustic signals incident upon said diaphragm, and wherein the channel provides an output signal indicative of the acoustic signals,
   wherein:
      said electret surface is disposed on said diaphragm in spaced, face-to-face relation to said channel; or
      said electret surface is disposed on said sensor member in spaced, face-to-face relation to an electrically conductive surface located on said diaphragm and disposed in spaced, face-to-face relation to said channel.

9. The electret microphone of claim 8, wherein said diaphragm defines a peripheral portion of said enclosed volume.

10. The electret microphone of claim 8, wherein said diaphragm extends across said enclosed volume to define a first portion of the enclosed volume on a first side of the diaphragm and a second portion of the enclosed volume on a second side of the diaphragm, and further comprising:
   at least one vent interconnecting said first portion and said second portion.

11. The electret microphone of claim 8, wherein the electret microphone includes an air gap between the diaphragm and the sensor member, and wherein said channel defines a first surface portion of the sensor member, and wherein said electret surface is disposed on a second surface portion of the sensor member that is spaced from said first portion thereof.

12. An electret microphone comprising:
   a first portion including a flexible diaphragm;
   a second portion including a sensor member including a semi-conductor channel; and
   an electret surface comprising a dielectric material having a permanently-embedded static electric charge, said electret surface being a part of the first portion or the second portion, wherein the channel of said sensor member has an electrical conductivity dependent upon relative movement of the first portion and second portion responsive to acoustic signals incident upon said diaphragm, and wherein the channel provides an output signal indicative of the acoustic signals,
   wherein the first portion does not contact the second portion, and
   wherein:
      said electret surface is disposed on said diaphragm in spaced, face-to-face relation to said channel; or
      said electret surface is disposed on said sensor member in spaced, face-to-face relation to an electrically conductive surface located on said diaphragm and disposed in spaced, face-to-face relation to said channel.

13. The electret microphone of claim 12, wherein said channel defines a first surface portion of the sensor member, and wherein said electret surface is disposed on a second surface portion of the sensor member that is spaced from said first surface portion thereof.

* * * * *